US00PP27603P2

(12) United States Plant Patent
Roberts

(10) Patent No.: US PP27,603 P2
(45) Date of Patent: Jan. 24, 2017

(54) MINT PLANT NAMED 'BLUE MOUNTAIN MINT'

(50) Latin Name: ***Mentha* sp.**
Varietal Denomination: Blue Mountain Mint

(71) Applicant: Essex Laboratories, Inc., Napavine, WA (US)

(72) Inventor: Donald D. Roberts, Independence, OR (US)

(73) Assignee: Essex Laboratories, LLC, Chehalis, WA (US)

( * ) Notice: Subject to any disclaimer, the term of this patent is extended or adjusted under 35 U.S.C. 154(b) by 0 days.

(21) Appl. No.: 14/999,509

(22) Filed: May 18, 2016

(51) Int. Cl.
*A01H 5/12* (2006.01)

(52) U.S. Cl.
USPC ..... Plt./259

(58) Field of Classification Search
USPC ..... Plt./259
CPC ..... A01H 5/12
See application file for complete search history.

(56) References Cited

PUBLICATIONS

Gobert, V., "Hybridization in the section *Mentha* (Lamiaceae) inferred from AFLP markers," Am. J. Bot., Dec. 2002, 89 (12), pp. 2017-2023.

Dung, Jeremiah K. S., et al., "Evaluation of Verticillium wilt resistance in *Mentha arvensis* and *M. longifolia* genotypes," Plant Disease, Oct. 2010, vol. 94, pp. 1255-1260.

Rohloff, Jens, et al., "Effect of harvest time and drying method on biomass production, essential oil yield, and quality of peppermint (*Mentha piperita* L.);" J. Agric. Food Chem., 2005, 53(10), pp. 4143-4148.

Rohloff, Jens, "Monoterpene composition of essential oil from peppermint (*Mentha piperita* L.) with regard to leaf position using solid-phase microextraction and gas chromatography/mass spectrometry analysis;" J. Agric. Food Chem., 1999, 47(9), pp. 3782-3786.

Verma, R. S., et al., "Essential oil composition of Menthol mint (*Mentha arvensis*) and peppermint (*Mentha piperita*) cultivars at different stages of plant growth from Kumaon Region of Western Himalaya," J. Medicinal and Aromatic Plants, 2010, vol. 1(1), pp. 13-18.

Roberts, D. D. and C. E. Horner, "Sources of resistance to Puccinia menthae in mint," Plant Disease, 1981, vol. 65(4), pp. 322-324.

*Primary Examiner* — Kent L Bell
(74) *Attorney, Agent, or Firm* — Marger Johnson

(57) ABSTRACT

Mint selection 14-27-71, denominated 'Blue Mountain Mint,' is a new *Mentha* sp. cultivar that produces an essential oil similar to commercial peppermint, produces more oil on a dry weight basis, and has resistance to mint rust (*Puccinia menthae*).

3 Drawing Sheets

Latin name of the genus and species: *Mentha* sp.
Variety denomination: 'BLUE MOUNTAIN MINT'.

FEDERAL SPONSORSHIP

None

TYPE OF PLANT AND NAME OF VARIETY

The present invention relates to a new and distinct variety of peppermint plant developed from a parent of the species *M. arvensis*. The new variety will be identified as 'Blue Mountain Mint.'

BACKGROUND OF INVENTION

'Blue Mountain Mint' originated as a seedling from an open pollinated commercial variety ('Blanco') of *Mentha arvensis*, included with other *M. arvensis* and male fertile *M. piperita* plants in a polycross breeding program. Commercial *M. piperita* is sterile and only becomes fertile in the polyploidy state. The parent plants in the polycross breeding system were composed of selected fertile male and female genotypes based on certain desirable characteristics.

DISCOVERY AND ASEXUAL REPRODUCTION

This new mint was developed in a mint breeding program in which the primary objective was to develop a Mitcham type peppermint variety having a specific oil composition, acceptable yield and resistant to mint diseases. The new variety is as susceptible to mint wilt (soil-borne fungus *Verticillium dahliae*) as its parent, but more resistant to mint rust (air-borne fungus *Puccinia menthae*). 'Blue Mountain Mint' has a higher yield of oil than the control variety, 'Black Mitcham,' in test plots since 2014. This plant was selected from a population of mint seedlings in research plots on land near Monmouth, Oreg., and initially identified as 14-27-71.

'Blue Mountain Mint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation with tip cuttings and stolon sections of 'Blue Mountain Mint' for greenhouse and field planting in Monmouth, Oreg., each year since 2014 and the genotype comes true to form with each generation.

SUMMARY OF THE INVENTION

Mint selection 14-27-71, denominated 'Blue Mountain Mint,' is a new *Mentha* sp. cultivar that produces a high yield of an essential oil similar in composition as commercially grown mint varieties. The essential oil is similar to standard *M. piperita* oil in components composition and ratio of components. Organoleptically it is similar to typical *Mentha piperita* peppermint oil. It is more resistant to mint rust than current commercially grown *Mentha arvensis* varieties known to the Inventor.

BRIEF DESCRIPTION OF THE FIGURES

The accompanying color figures show typical, one-year-old, greenhouse vegetative growth of 'Blue Mountain Mint' and depicts the color as nearly as reasonably possible.

FIG. 1 further illustrates the flower spike with capitate flower development at the nodes of the spike.

FIG. 2 illustrates the flower spike with capitate flower development at the nodes of the spike. FIG. 2 also illustrates the shape of the leaf (large leaf) collected at mid-plant and grown under greenhouse environment, whereas, the smaller leaf illustrates the shape of leaf on a terminal flowering shoot.

DESCRIPTION OF PLANT

Figure 1:
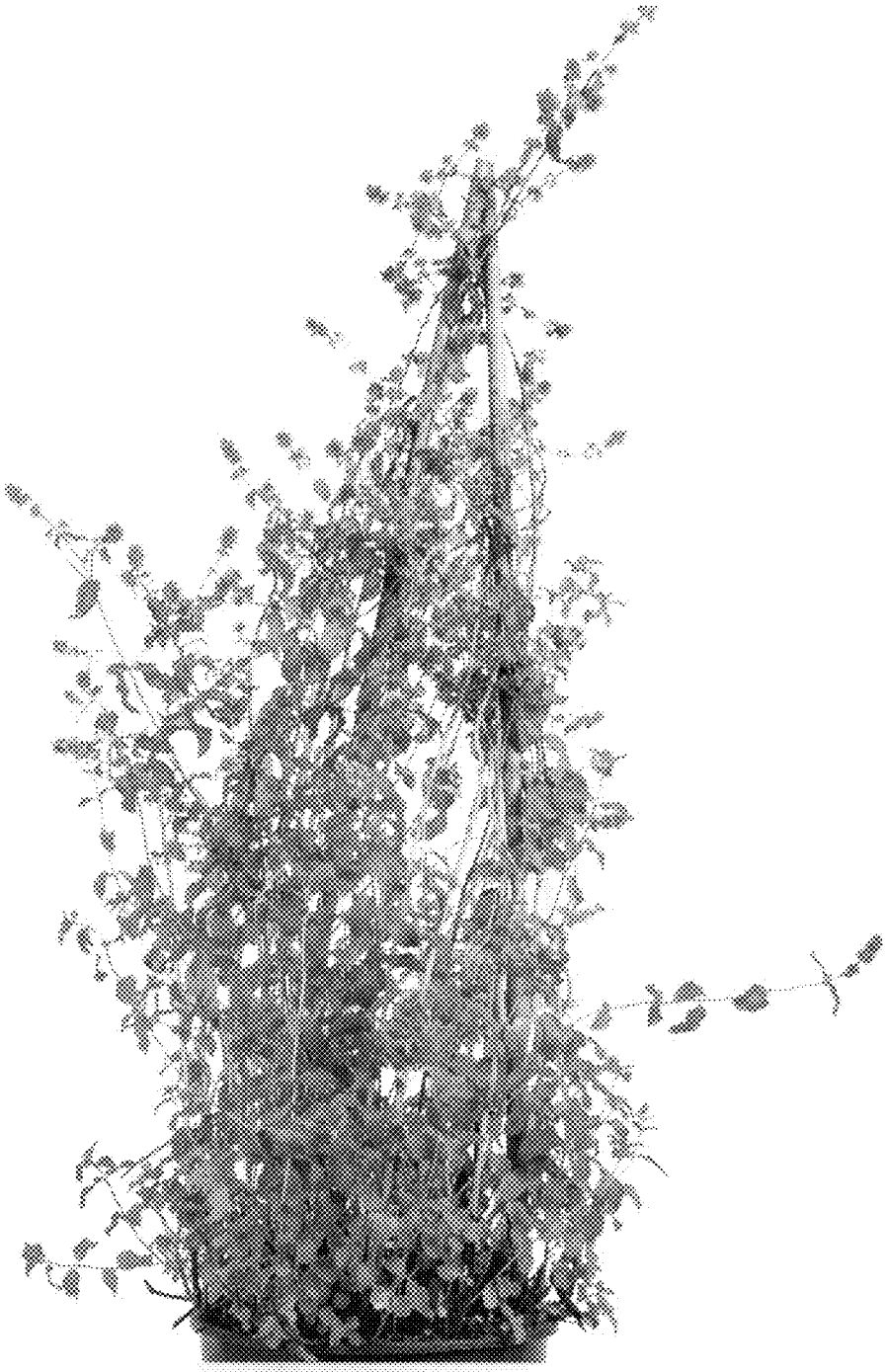
FIG. 1 illustrates the flowering pattern and multiple flowering shoots of my new mint plant in accordance with the present invention.

My new mint plant improves upon and is distinct from other mint plants known to the Inventor in several characteristics, including but not limited to, the following:

1. It increases yield of an essential oil similar in composition to typical commercial *M. piperita* known to the Inventor;
2. Produces more oil on a dry weight basis than currently grown mint varieties known to the Inventor;
3. A more vigorous plant growth with a branching pattern similar to its parent;
4. An early spring growth similar to 'Black Mitcham' peppermint but with an earlier maturity for desirable chemical composition of its essential oil;
5. A level of resistance to mint rust and mint wilt equal to or greater than that of its *M. arvensis* female parent;

The essential oil extracted from 'Blue Mountain Mint' has a composition of components more like that of commercial oil produced by 'Black Mitcham' peppermint (*M. piperita*) than that of *M. arvensis* as illustrated in Table 1. However, the ratio of oil components in 'Blue Mountain Mint' is different from that of its parent *M. arvensis*. The concentration of menthol in oil of 'Blue Mountain Mint' is less than that of its parent 'Blanco' *M. arvensis* and *M. piperita*. Menthofuran is present in the oil of 'Blue Mountain Mint' and absent in oil of its parent *M. arvensis*. Organoleptically, the oil of 'Blue Mountain Mint' is the same as that of 'Black Mitcham' but different than that of *M. arvensis*, reflecting the difference in oil component ratios.

TABLE 1

A Comparison of 'Blue Mountain Min' Essential Oil collected from test plots near Monmouth, Oregon, to that of its *M. arvensis* parent, Commercial *M. arvensis*, and Commercial *M. piperita* Oils. 1/

| Essential Oil Components | *Mentha arvensis* Parent Seedling | Blue Mountain Mint Seedling | Commercial *M. arvensis* | Commercial *M. piperita* |
|---|---|---|---|---|
| 1-Limonene | 3.0 | 1.7 | 3.0 | 1.7 |
| 1,8-Cineole | <1.0 | 4.9 | <1.0 | 4.9 |
| 1-Menthone | 15.7 | 18.5 | 7.3 | 19.4 |
| Menthofuran | 0.0 | 6.7 | 0.0 | 4.2 |
| Isomenthone | 3.5 | 2.4 | 3.6 | 3.1 |
| 1-Menthyl Acetate | 3.7 | 6.5 | 2.9 | 5.3 |
| 1-Menthol | 64.3 | 40.4 | 73.9 | 44.6 |
| Pulegone | <1.0 | 1.3 | 0.0 | 2.1 |

The numbers listed in the above table are percentages based upon the analysis of the respective mint oils by gas chromatography. The percentages are determined by calculation of the relative peak areas.

1/ Commercial oils of *M. arvensis* and *M. piperita* were samples of what is typically produced by mint growers. The essential oil from *M. arvensis* parent seedling and 'Blue Mountain Mint' were collected from plants growing in test plots in 2014.

TAXONOMIC DESCRIPTION OF 'BLUE MOUNTAIN MINT'

This new plant, under greenhouse and field growing conditions, is a bush type plant with lateral branches at each node of the main stems. The average height of 'Blue Mountain Mint' is 70-96 cm and is equal to or greater than 'Black Mitcham' growing under similar conditions and will vary based on fertilizer, soil quality, and water application, amongst other known factors that affect growth patterns. Secondary and tertiary branching occurs to form a compact growth habit. When 'Blue Mountain Mint' is mature and ready for harvest, the main stem at mid-plant (approximately between the eleventh and twelfth node) is 9.5-10.5 mm in width. The secondary and tertiary branch stems are 2.5-3.5 mm. The average plant width is 30 cm and the average length of the main stem is 76 cm. The stems are square, glabrous, and a green color that matches Fifth Edition Royal Horticultural Society Colour Chart 143B green group.

Figure 2:
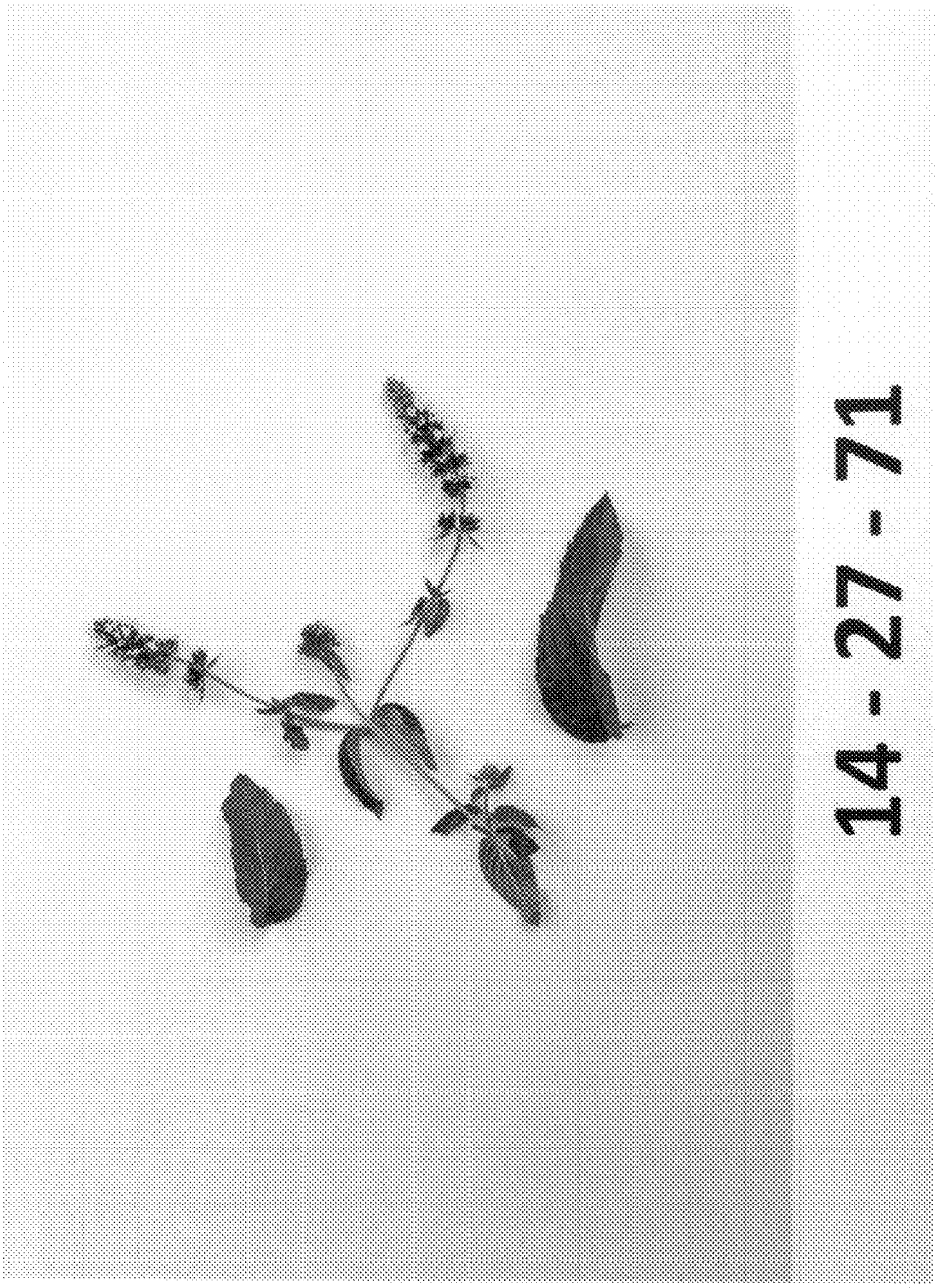
FIG. 2 illustrates the variance in leaf shape of my new mint plant depending on the location on the plant. Further.
Figure 3:
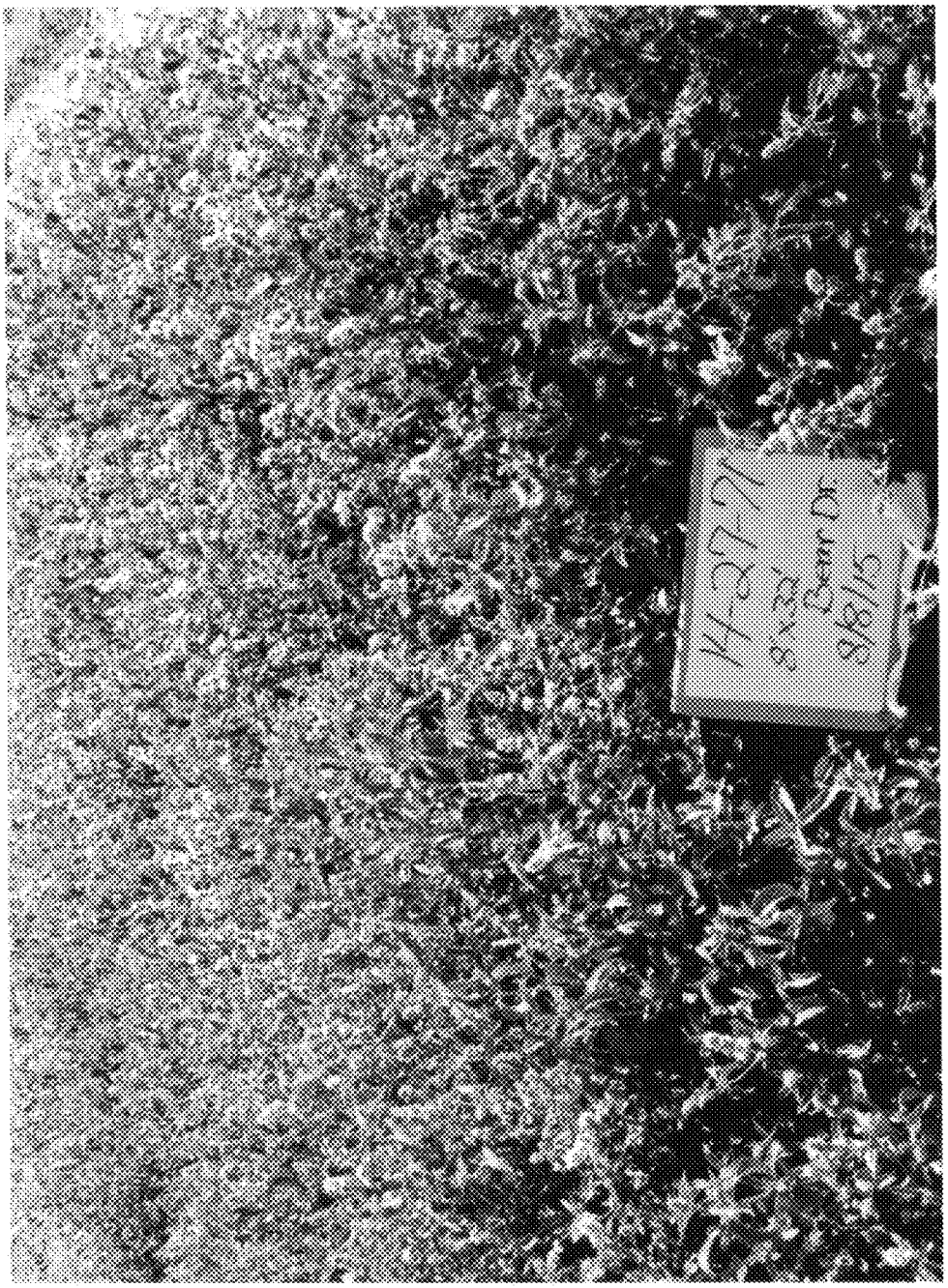
FIG. 3 illustrates the growth pattern under field management of my new mint plant in accordance with the present invention.

Mature leaves at the bottom of the plant are ovate as are leaves on secondary branch stems. Leaves on upper mature plants, both main and secondary stems are lanceolate (FIG. 2). Mid-main stem leaf size at flowering is 23-26 mm in width and 59-63 mm in length. Leaf size on secondary branches at flowering is 10-12 mm in width and 17-19 mm in length. Leaf petioles on the main stem leaves are 7-8 mm in length. Leaves on the mid-main and lower stem tend to be lanceolate and irregular denticulate while the leaves on the upper plant tend to be more dentate. The main stem leaves have from 11-13 teeth on each side while the secondary branch leaves have 4-5 teeth on each side. The adaxial leaf surface is glabrous and is light green in color, ranging from The Fifth Edition Royal Horticultural Society Colour Chart 143A to 143B in the green group classification. The abaxial leaf surface is sub-glabrous with oil glands distributed across the surface and is light green in color as illustrated in The Fifth Edition Royal Horticultural Society Colour Chart 143A green group. The leaf has 6-9 lateral veins, more or less in parallel off the main vein that runs from the petiole to the tip of the leaf. The veins are prominent in all leaves of 'Blue Mountain Mint.'

The inflorescence is a determinate spike with capitate flowers developing at the nodes of the spike stem. The cylindrical spikes are about 30 mm in diameter and range from 80-100 mm in length. The capitates flowers are 15-20 mm in width and 16-18 mm in length. The flowers consist of five petals fused into a two lipped corolla. The corolla is violet in color as illustrated in The Fifth Edition Royal Horticultural Society Colour Chart 91C to 91D in the violet-blue group. The calyx is generally green and ranges between 143B and 143C of The Fifth Edition Royal Horticultural Society Colour Chart, green group. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improved resistance to mint rust and a high yield of essential oil.

* * * * *

14 - 27 - 71